US008067404B2

(12) United States Patent
Roncucci et al.

(10) Patent No.: US 8,067,404 B2
(45) Date of Patent: Nov. 29, 2011

(54) PHTHALOCYANINE DERIVATIVES, PROCESS FOR THEIR PREPARATION, PHARMACEUTICAL COMPOSITIONS CONTAINING THEM AND THEIR USE

(75) Inventors: Gabrio Roncucci, Colle Val d'Elsa (IT); Giacomo Chiti, Prato (IT); Donata Dei, San Gimignano (IT); Annalisa Cocchi, Poggio a Caiano (IT); Lia Fantetti, Florence (IT); Stefano Mascheroni, Landriano (IT)

(73) Assignee: L. Molteni & C. Dei Fratelli Alitti Societa'di Esercizio S.p.A., Scandicci (IT)

( * ) Notice: Subject to any disclaimer, the term of this patent is extended or adjusted under 35 U.S.C. 154(b) by 996 days.

(21) Appl. No.: 11/913,532

(22) PCT Filed: May 4, 2006

(86) PCT No.: PCT/EP2006/062062
§ 371 (c)(1),
(2), (4) Date: Nov. 2, 2007

(87) PCT Pub. No.: WO2006/117399
PCT Pub. Date: Nov. 9, 2006

(65) Prior Publication Data
US 2009/0131392 A1 May 21, 2009

(30) Foreign Application Priority Data

May 5, 2005 (IT) ................ FI2005A0092

(51) Int. Cl.
*A61K 31/40* (2006.01)
*A61N 55/02* (2006.01)
*C07B 47/00* (2006.01)
*C07D 487/22* (2006.01)
(52) U.S. Cl. ...................... 514/185; 540/145
(58) Field of Classification Search .............. 540/145; 514/185
See application file for complete search history.

(56) References Cited

U.S. PATENT DOCUMENTS

| 5,281,616 | A | 1/1994 | Dixon et al. |
| 5,834,455 | A | 11/1998 | Russell et al. |
| 5,965,598 | A | 10/1999 | Roncucci et al. |
| 6,630,128 | B1 | 10/2003 | Love et al. |
| 7,144,879 | B2 * | 12/2006 | Roncucci et al. ............ 514/185 |

FOREIGN PATENT DOCUMENTS

| EP | 186404 A2 | 7/1986 |
| EP | 0 906 758 A1 | 4/1999 |
| EP | 0906758 | * 4/1999 |
| EP | 1164135 A1 | 12/2001 |
| EP | 1356813 A1 | 10/2003 |
| EP | 1381611 B1 | 1/2004 |
| WO | WO 02/090361 A1 | 11/2002 |
| WO | WO 03/037902 A1 | 5/2003 |

OTHER PUBLICATIONS

Mao et al, Science in China (Series B), vol. 41 No. 5, 1998.*
Fabris et al., Experimental Dermatology (2005), 14(9), 675-683.*
Hongjian et al., ACTA Physico-Chimica Sinica., vol. 12, No. I, Jan. 1996.*
Dummin, H. et al. (1997) "Selective photosensitization of mitochondria in hela cells by cationic zn(II) phthalocyanines with lipophilic side-chains" Journal of Photochemistry and Photobiology B: Biology 37:2319-229.
Griffiths, J. (1997) "Some observations on the synthesis of polysubstituted zinc phthalocyanine sensitisers for photodynamic therapy" Dyes and Pigments 33:65-78.
Hongjian et al. (1996) "Studies of the supramolecular system of prophyrin-phthalocyanine formed by molecular self-assembly and its photoinduced electron transfer process" Acta Physico Chimica Sinica 12:44-48.
Minnock, A. et al. (1996) "Photoinactivation of bacteria. Use of a cationic water-soluble zinc phthalocyanine to photoinactivate both gram-negative and gram-positive bacteria" Journal of Photochemistry and Photobiology B: Biology 32:159-164.
Wohrle, D. et al. (1990) "Synthesis of positively charged phthalocyanines and their activity in the photodynamic therapy of cancer cells" Photochemistry and Photobiology 51:351-356.
Ben-Hur, E. and Rosenthal, I. 1985 "The phthalocyanines: a new class of mammalian cells photosensitizers with a potential for cancer phototherapy" *Int J Radiat Biol Relat Stud Phys Chem Med* 47:145-147.

* cited by examiner

*Primary Examiner* — Paul V. Ward
(74) *Attorney, Agent, or Firm* — Knobbe Martens Olson & Bear LLP.

(57) ABSTRACT

Phthalocyanine derivatives are described having photosensitizing characteristics and high solubility in water, useful for photodynamic treatment of bacterial infections, in particular infections generated by Gram-negative bacteria.

31 Claims, No Drawings

PHTHALOCYANINE DERIVATIVES, PROCESS FOR THEIR PREPARATION, PHARMACEUTICAL COMPOSITIONS CONTAINING THEM AND THEIR USE

RELATED APPLICATIONS

This application is a U.S. National Phase of International application PCT/EP2006/062062, filed May 4, 2006, designating the U.S. and published in English on Nov. 9, 2006 as WO 2006/117399, which claims the benefit of Italian application No. FI2005A00092 filed May 5, 2005.

FIELD OF THE INVENTION

The invention relates to the field of photosensitising compounds for therapeutic use, and in particular to novel phthalocyanine derivatives of formula (I) given hereinafter, having photosensitising characteristics and high solubility in water, useful for the photodynamic treatment of bacterial infections, in particular infections generated by Gram-negative bacteria.

STATE OF THE ART

Molecules containing the phthalocyanine chromofluorophore macrocycle are known to produce reactive oxygen species, such as radicals or singlet oxygen, by interacting with visible light.

Because of these properties, phthalocyanine compounds have long been used in photodynamic therapy (hereinafter abbreviated to "PDT") for both therapeutic treatment and diagnostic purposes.

Examples of said compounds are described by Ben-Hur E. et al. in *Int. J Radiat. Biol.*, Vol. 47, 145-147 (1985). Other photosensitising agents useful in PDT are zinc phthalocyanine complexes and their conjugates described in U.S. Pat. No. 5,965,598, in the name of the Applicant. These compounds have proved to be effective photosensitising agents in PDT treatment for both tumours and microbial infections. The photodynamic activity generally demonstrated by the phthalocyanine derivatives described in U.S. Pat. No. 5,965,598 against Gram-negative bacteria is however generally lower than that against Gram-positive bacteria. This is consistent with the knowledge acquired to date that Gram-negative bacteria (*Escherichia coli, Pseudomonas aeruginosa*, etc.) are more resistant than Gram-positive bacteria (*Staphylococcus aureus, Streptococcus pyogenes*, etc.) to photosensitising agents. According to a number of studies on the subject, this greater resistance is associated with the outer bacterial cell walls of the Gram-negative bacteria being structurally different from Gram-positive bacteria.

The need was therefore felt to identify photosensitising compounds that combine high phototoxicity with a greater penetration and localisation capacity in Gram-negative bacteria, which would result in their increased effectiveness in photodynamic therapy (PDT) for infections caused by this type of bacteria.

SUMMARY OF THE INVENTION

The Applicant has now found that the novel tetrasubstituted phthalocyanine derivatives of formula (I) given hereinafter, besides having a high phototoxic efficiency, also possess photobleaching kinetics such as to ensure that the phosensitiser remains unaltered for a time sufficient for microbial photoinactivation and subsequent decomposition, thus avoiding toxicity by systemic absorption and induction of delayed phototoxicity.

Moreover, they have showed particularly high solubility in water, thus ensuring good bio-availability and fast metabolism within the organism. Consequently, said phthalocyanine derivatives are useful for the photodynamic treatment of bacterial infections caused by Gram-negative bacteria.

Subject of the invention are therefore the phthalocyanine derivatives of formula (I)

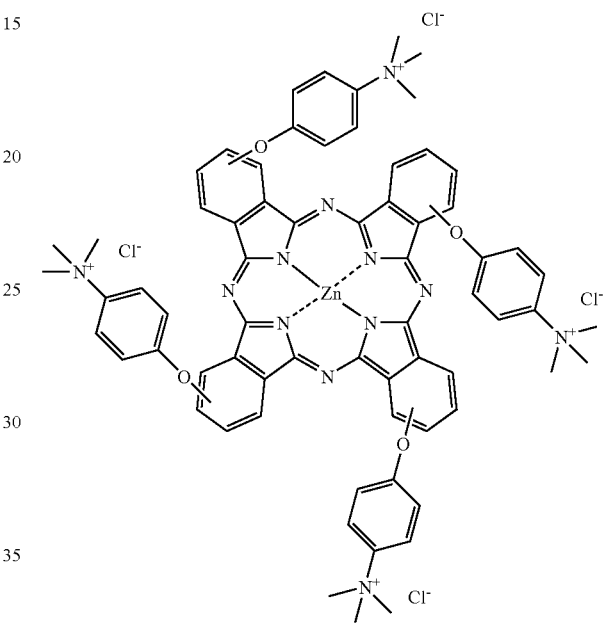

(I)

in which the substituents are in positions 1,8(11), 15(18), 22(25) or in positions 2,9(10), 16(17), 23(24) of the phthalocyanine ring.

Further subjects of the invention are the pharmaceutical compositions comprising as active principle a phthalocyanine derivative of formula (I) as aforedescribed, possibly in combination with metal chelating agents, the use of these derivatives for the preparation of pharmaceutical compositions for treating by photodynamic therapy bacterial infections caused by Gram-negative bacteria and mixed infections, the process for preparing the derivatives of formula (I), and the novel intermediates of formula (V), (VI) and (VII) which form in the process.

The characteristics and advantages of the invention will be illustrated in detail in the following description.

DETAILED DESCRIPTION OF THE INVENTION

The derivatives of formula (I) in accordance with the invention, although included in the general formula given in U.S. Pat. No. 5,965,598, were not specifically identified therein. The present derivatives have also demonstrated a surprising effectiveness in photodynamic therapy PDT against bacterial infections due to Gram-negative bacteria, unexpectedly higher than similar products described in the aforesaid US patent. The particular antibacterial activity towards Gram-negative bacteria makes them useful for treating bacterial infections caused by this type of micro-organisms alone, and for treating mixed infections due in part to Gram-negative bacteria and in part to other bacterial species.

Their solubility in water has also proven to be surprisingly high, with a consequent higher bio-availability and faster metabolism within the organism compared to similar products described in U.S. Pat. No. 5,965,598.

The present products of formula (I) have the ability to localise onto target cells where, following irradiation with light of determined wavelength, they produce reactive species which damage the cell itself. Because of their short duration these reactive species hit the target cell and damage it without any possibility of their spreading to nearby cells, while those that do not hit the biological target rapidly decay. By virtue of using said products, PDT therapy is therefore selective and does not lead to the phenomena of systemic or local skin phototoxicity.

The phthalocyanine derivatives of the invention possess a higher molar extinction coefficient than the photosensitising agents currently used in therapy, this guaranteeing effective therapeutic response. The present products are moreover activated by tissue penetrating radiation which has a wavelength longer than 650 nm and are therefore suitable for applications in PDT therapy against localised infections, whether dermatological or of mucosal surfaces, as well as deep seated infections due to the penetration characteristics of these radiations; when irradiated, they induce the production of reactive oxygen species even in conditions of low oxygenation, this being an important requisite for products that have to enable specific treatment against anaerobic micro-organisms, well known to proliferate in oxygen poor environments.

In the absence of light radiation, the products of the invention have a limited toxicity against host tissues and/or cells, but they re-activate if irradiated once more in a continuous production process of reactive species.

Sources of light suitable for carrying out the PDT treatment are known in the art and comprise white light, suitably filtered non-coherent sources at a wavelength of preferably between 650 and 750 nm or lasers specific for the wavelength of the present compounds. The total quantity of light radiation used varies according to the treatment and the tissues to be treated, and generally it is comprised between 50 and 1000 J/cm$^2$, preferably between 100 and 350 J/cm$^2$.

In particular, the products of the invention have showed a particularly good effectiveness against Gram-negative bacteria in contrast to other products of very similar structure which, though effective for example against Gram-positive bacteria however demonstrate a lower photodynamic activity against Gram-negative bacteria compared with the present products.

The present phthalocyanine derivatives can be prepared starting from commercial products by the following process, also subject of the invention. The present process comprises the following steps:

i) nucleophilic substitution of the amino alcohol of formula (III) onto the phthalonitrile of formula (II) to obtain the compound of formula (IV)

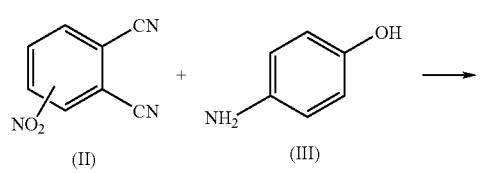

(II)  (III)

ii) reductive methylation of the amino nitrogen on the compound of formula (IV) coming from step i) to obtain the compound of formula (V)

iii) base catalysed tetramerization of the compound of formula (V) coming from step ii) and simultaneous metal insertion with a suitable Zinc(II) salt to obtain the Zinc(II) phthalocyanine of formula (VI)

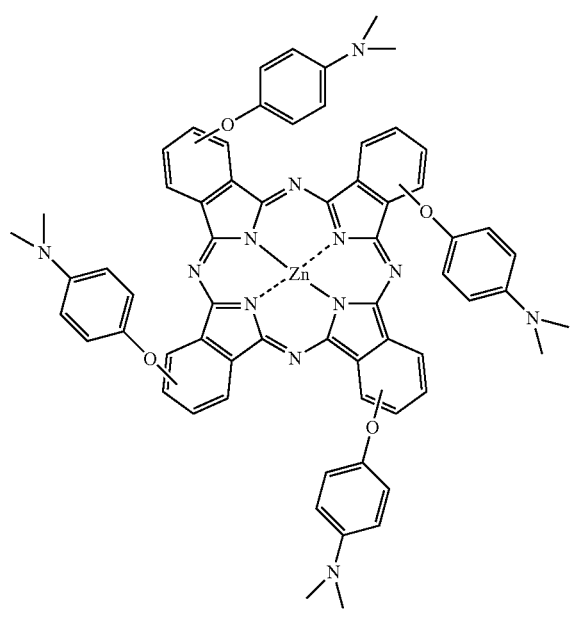

(VI)

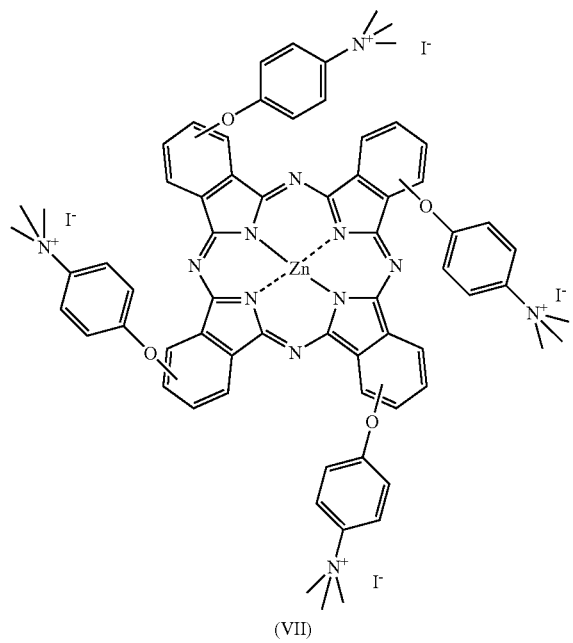

(VII)

iv) quaternarization of the amino groups of the phthalocyanine of formula (VI) coming from step iii) by treatment with methyl iodide to obtain the corresponding phthalocyanine of formula (VII) substituted with quaternary ammonium groups and in iodide form:

v) treatment of the phthalocyanine of formula (VII) in iodide form coming from step iv) with a suitable ion exchange resin to obtain the corresponding phthalocyanine of formula (I) in chloride form:

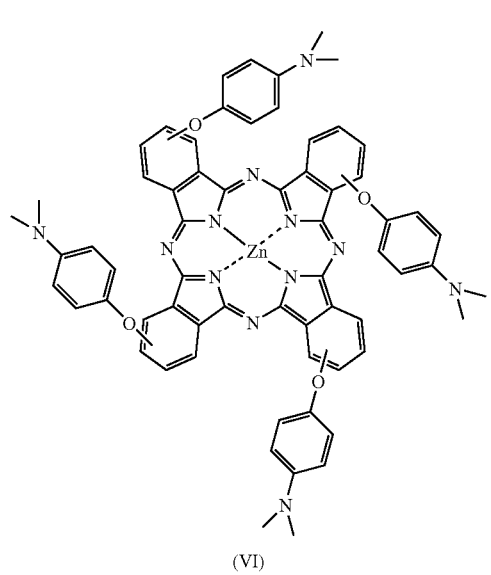

(VI)

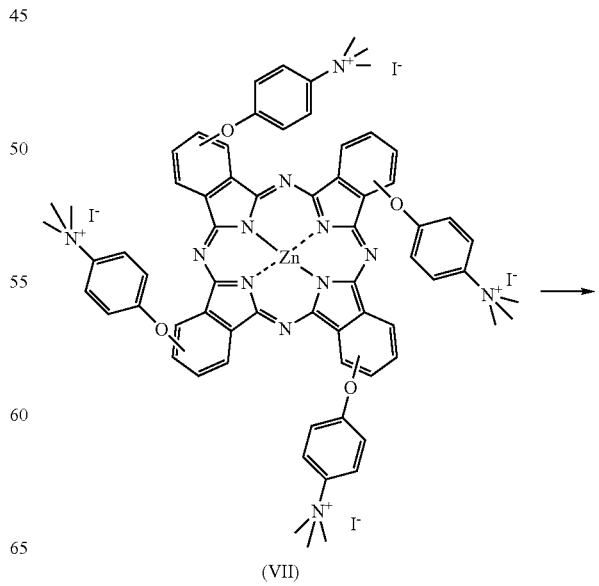

(VII)

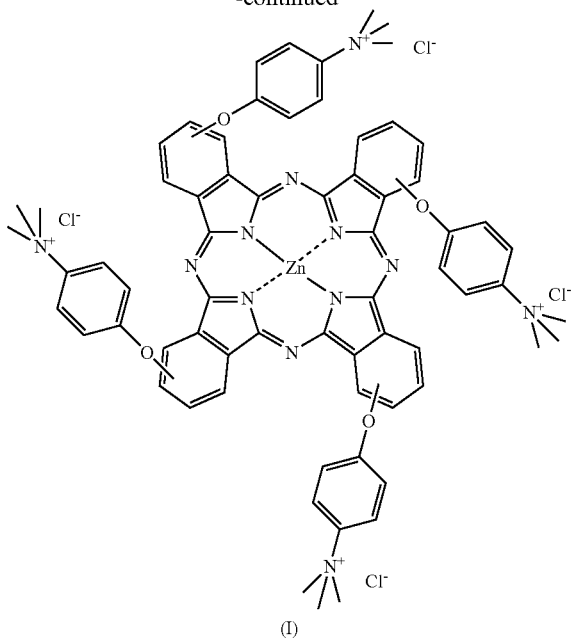

(I)

As far as the Applicant's knowledge extends, the processes for preparing substituted Zinc phthalocyanines described in the literature to date, for example the process described in U.S. Pat. No. 5,965,598, are not suitable for preparing the chlorides such as the present compounds of formula (I).

Step ii) of reductive methylation can be carried out for example by treating the primary amine of formula (IV), dissolved in a suitable solvent, with a carbonylating agent in the presence of a reducing agent; preferred conditions are those in which the amine (IV), dissolved in acetonitrile, is treated with 30% aqueous formaldehyde and sodium cyanoborohydride.

Step iii) of the process of the invention can be carried out in an organic solvent, preferably water miscible such as dimethylformamide (hereinafter abbreviated to DMF), using as the base a base chosen from 1,5-diazabicyclo[5.4.0]non-5-ene (hereinafter abbreviated to DBN), 1,8-diazabicyclo[5.4.0]undec-7-ene (hereinafter abbreviated to DBU) and 2-dimethylamino-ethanol (hereinafter abbreviated to DMAE), or, preferably, step iii) is carried out in the absence of solvent with a base chosen from the aforementioned.

The reaction times vary according to the scale of synthesis, while the temperatures can vary from 100 to 250° C., preferably between 130 and 180° C.

Optimal results are obtained when step iii) is carried out in the absence of solvents, with DBU as the base, and at a temperature equal to 140° C.

The crude product of formula (VI) is preferably precipitated by treating the reaction mixture of step iii) with water, filtering or centrifuging the suspension then washing the recovered solid several times with water and methanol.

The intermediate (VI) coming from step iii) is preferably purified by column chromatography followed by re-precipitation from solvent prior to undergoing the subsequent step. The stationary phase for the chromatography is for example silica gel, while the mobile phase is a mixture of dichloromethane and methanol; for the re-precipitation, dichloromethane for example can be used as the solvent and n-hexane as the precipitant.

In accordance with a preferred embodiment of the invention, at step iv) of the present process the methyl iodide is used in a quantity between 1 and 20 equivalents per amino group to be methylated, preferably in a quantity between 5 and 11 equivalents. The methylation reaction is furthermore typically carried out in a solvent, preferably selected from the group consisting of DMF, dimethylsulfoxide (hereinafter abbreviated to DMSO) and N-methylpyrrolidone (hereinafter abbreviated to NMP).

Preferred is the process wherein step iv) of the methylation is carried out using from 5 to 11 equivalents of methyl iodide per amino group, and NMP as the solvent.

The term "suitable Zinc(II) salt" in step iii) means for example Zinc(II) chloride or Zinc(II) acetate, preferably Zinc (II) acetate.

In accordance with a particularly preferred embodiment of the present process, the product of formula (VII) is precipitated from the solution in NMP with ethyl ether or isopropyl ether in a quantity of 8 volumes with respect to the volume of NMP, after having diluted the solution in NMP with methanol in a quantity of 2 volumes with respect to the volume of NMP.

The exchange of iodide for chloride at step v) of the present process is preferably undertaken by a chromatography process by using a solution of the iodide and an ion exchange resin and recovering the product from the solution by evaporation, lyophilisation or precipitation. Ion exchange resins suitable for undertaking the present process are strong basic resins, with quaternary ammonium functional groups, for example a polystyrene based resin with a degree of cross-linking between 4 and 10%, such as Amberlite® IRA-400 (CI) resin.

In accordance with a preferred embodiment of the process of the invention, step v) is carried out by a chromatography process by using a solution in methanol of the iodide of formula (VII) and a suitable resin, then treating the eluate with ethyl ether to precipitate the desired chloride of formula (I).

In accordance with a preferred embodiment of the process of the invention, when the ion exchange resin is used, step v) is carried out by a chromatography process by using a solution of the iodide of formula (VII) in a 8/2 mixture of methanol/DMSO and a suitable resin, then re-precipitating from the eluate the obtained chloride of formula (I) by treating it with ethyl ether and purifying it from the residual DMSO by dissolving in methanol and re-precipitating by adding ethyl ether.

A preferred aspect of the process is the use of an eluent based on methanol rather than water for the ion exchange chromatography in step v). In this respect, with the afore-described process, the final chloride is found to be further purified from related compounds present, achieving a HPLC purity greater than 98%.

The present products can be used as active principles in combination with pharmaceutically acceptable excipients and diluents for preparing pharmaceutical compositions, such as for parenteral administration and topical application.

The compositions can be formulated for example as aqueous solutions, lotions, creams, ointments or gels. In these pharmaceutical compositions, dosages of the active principle can vary for example between 0.1 and 20 mg of product of formula (I) per Kg body weight, preferably varying between 0.2 and 5 mg per Kg body weight.

Particularly preferred are pharmaceutical compositions of the invention comprising, in addition to a product of formula (I), a metal chelating agent, chosen preferably among metal chelating agents having specificity for $Ca^{2+}$ and $Mg^{2+}$ ions, such as citric acid, 1,2-diaminocyclohexane-N,N,N',N'-tetraacetic acid (CDTA), diethylenetriaminepentaacetic acid (DTPA) or ethylenediamine-N,N,N',N'-tetraacetic acid (EDTA). Particularly preferred are compositions comprising EDTA. The following non-limiting example of the present invention is given by way of illustration.

EXAMPLE 1

Preparation of the Phthalocyanine Derivative of Formula (I) in which the Substituents are in Positions 1,8(11), 15(18), 22(25) of the Phthalocyanine Ring a) Synthesis of 3-(4-aminophenoxy)phthalonitrile 160 g of 3-nitrophthalonitrile (0.92 mol) and 150.4 g of 4-aminophenol (1.37 mol) are dissolved in 2.5 l of dimethylsulfoxide (DMSO), then 384 g of $K_2CO_3$ (2.77 mol) are added.

The reaction mixture thus obtained is maintained for 22 hours under vigorous stirring at room temperature, then treated with 11.2 l of deionised $H_2O$ and maintained for 30 minutes under stirring.

The suspension thus obtained is filtered and the solid washed with deionised $H_2O$ (2×2 l).

After drying, 213.6 g of a solid product are obtained, found to be 3-(4-aminophenoxy)phthalonitrile (yield=98.7%). The product was characterised by melting point and $^1$H-NMR analysis:

$^1$H-NMR (300 MHz, DMSO-$d_6$): δ ppm=7.78-7.71 (m, 2H), 7.10 (dd, 1H, J=7.8 Hz, J=2.0 Hz), 6.89 (d, 2H, J=8.8 Hz), 6.62 (d, 2H, J=8.8 Hz), 5.28 (bs, 2H).

m.p.=188-191° C.

b) Synthesis of 3-(4-N,N-dimethylaminophenoxy)phthalonitrile 100 g of 3-(4-aminophenoxy)phthalonitrile (0.41 mol) obtained as aforedescribed in paragraph a) are dissolved in 2.6 l of $CH_3CN$.

The mixture is placed under stirring and 400 ml of a 30% aqueous formaldehyde solution are added. Maintaining the mixture at 0° C., 132 g of $NaBH_3CN$ (2.1 mol) and 80 ml of glacial acetic acid are added until the pH=6.8.

The mixture thus obtained is heated to 50° C. and maintained under hot conditions and under stirring for 22 hours. After this period, the mixture is brought again to room temperature, treated with 12 l of deionised $H_2O$ and maintained under stirring for 30 minutes then the suspension obtained is filtered and the solid washed with deionized $H_2O$ (2×2 l).

After drying, 107.8 g of a solid product are obtained found to be 3-(4-N,N-dimethylaminophenoxy)phthalonitrile (yield=96.3%). The product was characterised by melting point and $^1$H-NMR analysis:

$^1$H-NMR (300 MHz, DMSO-$d_6$): δ ppm=7,76-7,74 (m, 2H), 7,12-7,06 m, 3H), 6,79 (d, 2H, J=8.9 Hz), 2.90 (s, 6H).

m.p.=160-162° C.

c) Synthesis of Zinc(II) [1,8(11), 15(18), 22(25)-tetrakis-(4-N,N-dimethylamino phenoxy)] Phthalocyaninate Under nitrogen atmosphere, 80 g of 3-(4-N,N-dimethylaminophenoxy)phthalonitrile (0.3 mol) obtained as aforedescribed in paragraph b) are dissolved in 460 ml of DBU (3 mol).

28 g of $Zn(AcO)_2$ (0.15 mol) are added to the solution thus obtained and the reaction mixture is then brought to 140° C. and maintained at this temperature, shielded from light, under nitrogen atmosphere and under vigorous stirring for 22 hours. After this period, the mixture is brought again to room temperature then treated with 14 l of deionized $H_2O$ and the suspension is filtered, washing the solid with $H_2O$ (2×2 l) and MeOH (1×1 l). The product thus obtained was purified by silica gel chromatography (mobile phase: $CH_2Cl_2$/MeOH from 98/2 to 95/5), then re-precipitating from solvent by dissolving the product derived from the chromatography in 0.5 l of $CH_2Cl_2$ and re-precipitating it by adding 4 l of n-hexane.

After filtering, washing with n-hexane (2×1 l) and drying, 60.1 g of product are obtained found to be Zinc(II) [1,8(11), 15(18), 22(25)-tetrakis-(4-N,N-dimethylamino phenoxy)] phthalocyaninate (yield=72.3%). The product was characterised by $^1$H-NMR analysis.

$^1$H-NMR (300 MHz, DMSO-$d_6$): δ ppm=9.20-8.75 (m, 4H), 8.19-7.96 (m=4H), 7.59-6.70 (m, 20H), 2.93-2.90 (m, 24H).

d) Synthesis of Zinc(II) [1,8(11), 15(18), 22(25)-tetrakis-(4-N,N,N-trimethylammonium phenoxy)] Phthalocyaninate Tetraiodide 60 g of Zinc(II) [1,8(11), 15(18), 22(25)-tetrakis-(4-N,N-dimethylaminophenoxy)] phthalocyaninate (0.054 mol) obtained as aforedescribed in paragraph c) were dissolved in 1.5 l of N-methylpyrrolidone (NMP).

150 ml of MeI (2.4 mol) are then added and the solution is maintained at room temperature, shielded from light, under stirring and under nitrogen atmosphere for 72 hours. The reaction mixture thus obtained is diluted with 3 l of MeOH, then treated with 12 l of isopropyl ether. After treatment, the suspension obtained is left under stirring for ½ hour and allowed to stand for 1 hour, then filtered and the solid washed with isopropyl ether (2×2 l) and ethyl ether (2×2 l). 94.7 g of wet product are obtained used as such for the next step after dividing into two sub-batches.

The product was characterised by $^1$H-NMR.

$^1$H-NMR (300 MHz, DMSO-$d_6$): δ ppm=9.49-7.31 (m, 28H), 3.67-3.55 (m, 36H).

e) Synthesis of Zinc(II) [1,8(11), 15(18), 22(25)-tetrakis-(4-N,N,N-trimethylammonium phenoxy)] Phthalocyaninate Tetrachloride The 2 sub-batches of Zinc(II) [1,8(11), 15(18), 22(25)-tetrakis-(4-N,N,N-trimethylammonium phenoxy)] phthalocyaninate tetraiodide obtained as aforedescribed in paragraph d), each equal to 47.2 g, are processed as follows. 47.2 g of the aforesaid product are dissolved in 2 l of 4/1 MeOH/DMSO. The solution is subjected to column chromatography whose stationary phase is prepared with 470 g of Amberlite® IRA 400 (Cl) resin, previously washed with an aqueous solution made acid by 0.5 M HCl and conditioned with 4/1 MeOH/DMSO. 12 l of ethyl ether are slowly added to the eluate, maintained under stirring. The suspension obtained is left to stand for 1 hour, then filtered and the solid washed with ethyl ether (4×0.5 l).

From the two procedures, 31.1 g and 32.1 g of wet product are obtained which are combined and re-precipitated by dissolving in 3 l of MeOH, then slowly adding 12 l of ethyl ether to the solution obtained while maintaining under stirring. The suspension is left to stand for 1 hour, then filtered and the solid washed with ethyl ether (4×0.5 l).

After drying, 57.8 g of the title product are obtained, characterised as follows.

$^1$H-NMR (300 MHz, DMSO-$d_6$): δ ppm=9.46-7.29 (m, 28H), 3.70-3.57 (m=36H).

$^{13}$C-NMR (75 MHz, DMSO-$d_6$): δ ppm=160.36 160.23 158.78 158.64 158.51 158.26 153.90 153.29 153.12 152.7 152.43 152.19 151.60 150.03 149.65 143.33 143.08 142.90 141.90 141.67 132.12 131.66 131.26 129.25 129.05 128.48 128.19 123.76 123.16 121.37 120.85 120.48 118.88 117.59 117.31 57.24 57.09.

UV-vis (MeOH/H$_2$O 50/50) $\lambda_{max}$(%): 690 (100), 622 (18), 340(23).

ESI-MS: m/z 294,1 [(M-4Cl)$^{4+}$].

The invention claimed is:

1. A phthalocyanine compound of formula (I)

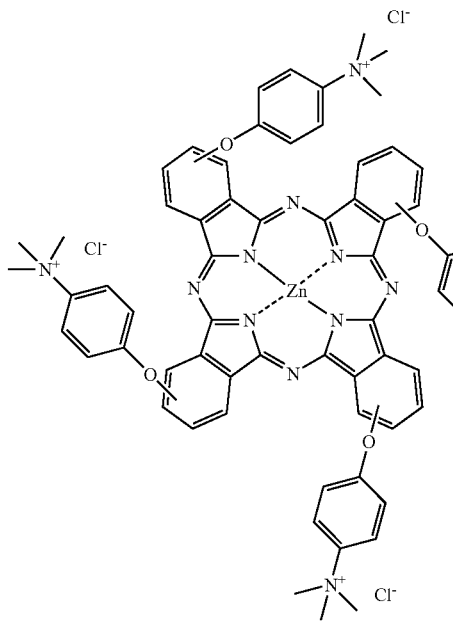

(I)

in which the substituents are in positions 1,8(11), 15(18), 22(25) or in positions 2,9(10), 16(17), 23(24) of the phthalocyanine ring.

2. Process for preparing a phthalocyanine compound of formula (I) as defined in claim 1, comprising the following steps:

i) performing nucleophilic substitution of the amino alcohol of formula (III) onto the phthalonitrile of formula (II) to obtain the compound of formula (IV)

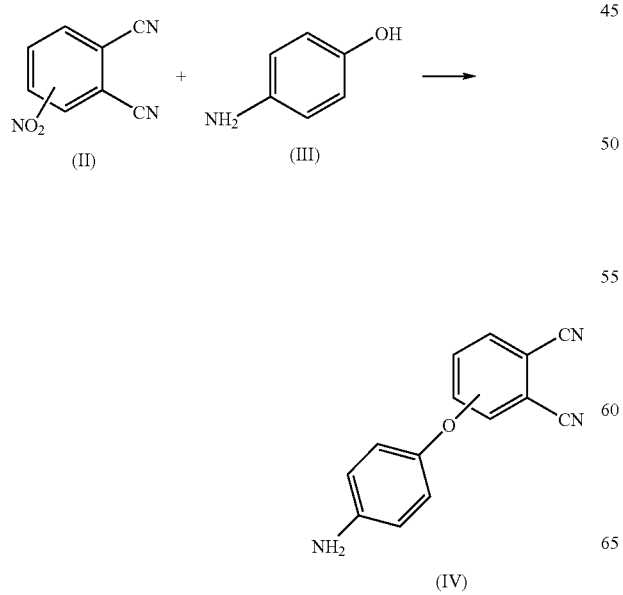

ii) performing reductive methylation of the amino nitrogen on the compound of formula (IV) coming from step i) to obtain the compound of formula (V)

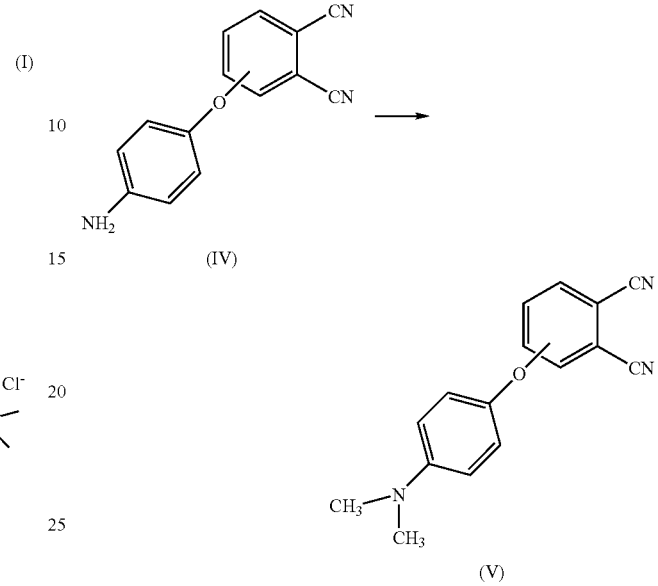

iii) performing base catalysed tetramerization of the compound of formula (V) coming from step ii) and simultaneous metal insertion with a suitable Zinc(II) salt to obtain the Zinc(II) phthalocyanine of formula (VI)

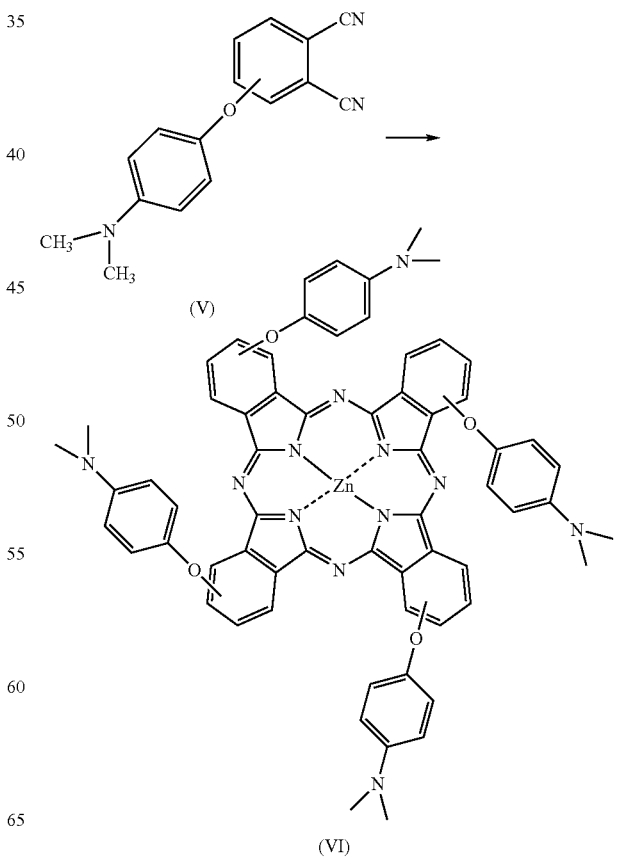

iv) performing quaternarization of the amino groups of the phthalocyanine of formula (VI) coming from step iii) by treatment with methyl iodide to obtain the corresponding phthalocyanine of formula (VII) substituted with quaternary ammonium groups and in iodide form:

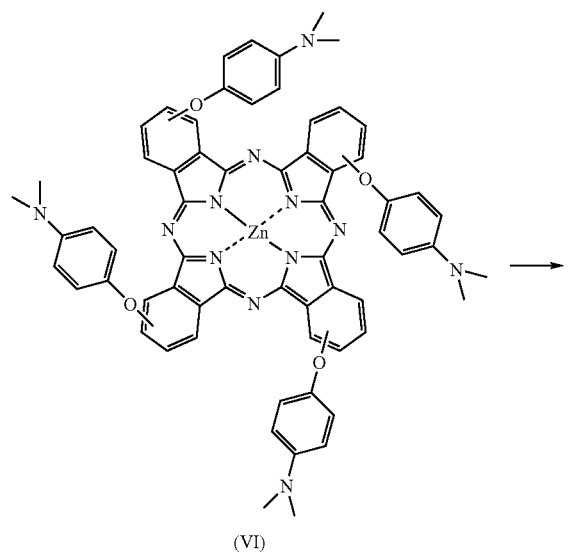

(VI)

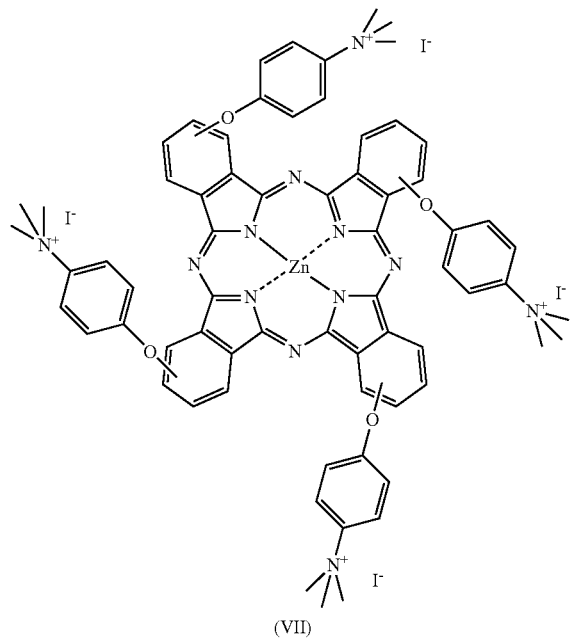

(VII)

v) performing treatment of the phthalocyanine of formula (VII) in iodide form coming from step iv) with a suitable ion exchange resin to obtain the corresponding phthalocyanine of formula (I) in chloride form:

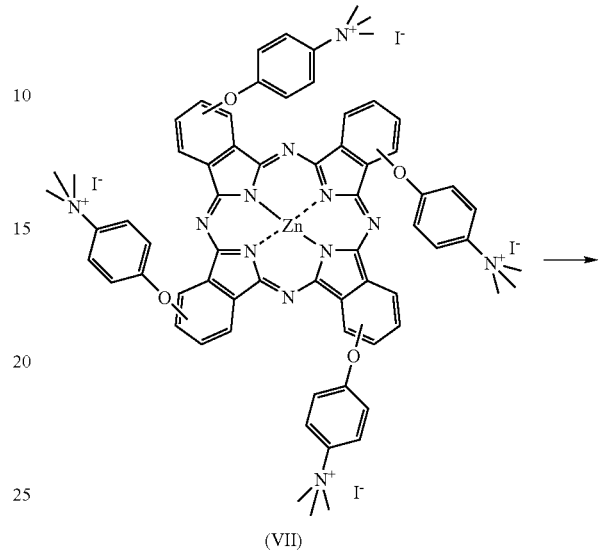

(VII)

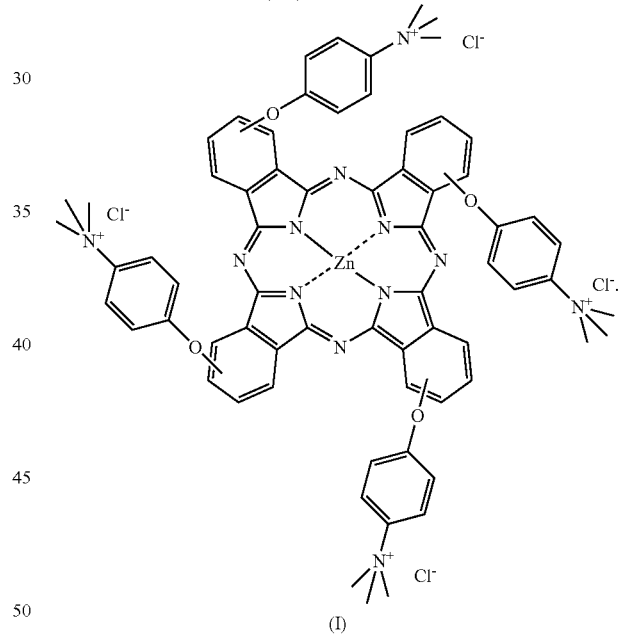

(I)

3. Pharmaceutical compositions comprising as active principle a phthalocyanine compound of formula (I) as defined in claim 1, in combination with pharmaceutically acceptable excipients and/or diluents.

4. The pharmaceutical compositions according to claim 3, further comprising a metal chelating agent.

5. The pharmaceutical compositions according to claim 4, wherein said metal chelating agent is chosen from metal chelating agents having specificity for $Ca^{2+}$ and $Mg^{2+}$ ions.

6. The pharmaceutical compositions according to claim 4, wherein said metal chelating agent is selected from the group consisting of citric acid, 1,2-diaminocyclohexane-N,N,N',N'-tetraacetic acid (CDTA), diethylenetriaminepentaacetic acid (DTPA) and ethylenediamine-N,N,N',N'-tetraacetic acid (EDTA).

7. The pharmaceutical compositions according to claim 4, wherein said metal chelating agent is EDTA.

8. Compounds of formula (V), (VI) and (VII) as intermediates of the process as defined in claim 2.

9. The process according to claim 2, wherein said step ii) of reductive methylation is carried out by treating said compound of formula (II), dissolved in acetonitrile, with 30% aqueous formaldehyde in the presence of sodium cyanoborohydride.

10. The process according to claim 2, wherein said step iii) is carried out at a temperature between 100 and 250° C.

11. The process according to claim 10, wherein said temperature is between 130 and 180° C.

12. The process according to claim 2, wherein said step iii) is carried out in an organic solvent, using as the base a base chosen from 1,5-diazabicyclo[5.4.0]non-5-ene (DBN), 1,8-diazabicyclo[5.4.0]undec-7-ene (DBU) and 2-dimethylamino-ethanol (DMAE).

13. The process according to claim 2, wherein said step iii) is carried out in the absence of solvent, using as the base a base chosen from 1,5-diazabicyclo[5.4.0]non-5-ene (DBN), 1,8-diazabicyclo[5.4.0]undec-7-ene (DBU) and 2-dimethylamino-ethanol (DMAE).

14. The process according to claim 2, wherein said step iii) is carried out in the absence of solvent with DBU as base, and at a temperature of 140° C.

15. The process according to claim 2, wherein the crude product of formula (VI) obtained in step iii) is precipitated by treating the reaction mixture with water, filtering or centrifuging the suspension and washing the recovered solid several times with water and methanol.

16. The process according to claim 2, further comprising the purification of the intermediate of formula (VI) coming from step iii) by column chromatography followed by re-precipitation from solvent, prior to undergoing step iv).

17. The process according to claim 16, wherein said column chromatography is carried out using silica gel as the stationary phase and a mixture of dichloromethane and methanol as the mobile phase; said re-precipitation is carried out using dichloromethane as the solvent and n-hexane as the precipitant.

18. The process according to claim 2, wherein said methylating agent in step iv) is methyl iodide.

19. The process according to claim 18, wherein said methyl iodide is used in a quantity between 1 and 20 equivalents per amino group to be methylated in the product of formula (VI).

20. The process according to claim 18, wherein said methyl iodide is used in a quantity between 5 and 11 equivalents per amino group to be methylated in the product of formula (VI).

21. The process according to claim 2, wherein said methylation reaction in step iv) is carried out in a solvent chosen from dimethylformamide, dimethylsulfoxide and N-methylpyrrolidone.

22. The process according to claim 21, wherein said solvent is N-methylpyrrolidone.

23. The process according to claim 2, wherein said methylation reaction in step iv) is carried out using methyl iodide as the methylating agent in a quantity between 5 and 11 equivalents per amino group to be methylated in the product of formula (VI), and N-methylpyrrolidone as solvent.

24. The process according to claim 23, wherein the reaction product in step iv) is precipitated from the solution in N-methylpyrrolidone with ethyl ether or isopropyl ether in a quantity of 8 volumes with respect to the volume of N-methylpyrrolidone, after having diluted the solution in N-methylpyrrolidone with methanol in a quantity of 2 volumes with respect to the volume of N-methylpyrrolidone.

25. The process according to claim 2, wherein said Zinc(II) salt in step iii) is chosen from Zinc(II) chloride and Zinc(II) acetate.

26. The process according to claim 2, wherein said Zinc(II) salt in step iii) is Zinc(II) acetate.

27. The process according to claim 2, wherein said ion exchange resin in step v) is chosen from strong basic resins with quaternary ammonium functional groups.

28. The process according to claim 27, wherein said resin is a resin based on polystyrene with a degree of cross-linking between 4 and 10%.

29. The process according to claim 2, wherein said treatment of the phthalocyanine (VII) in step v) is achieved by a chromatography process by using a solution of said phthalocyanine (VII) and said ion exchange resin, and recovering the phthalocyanine of formula (I) by evaporation, lyophilisation or precipitation.

30. The process according to claim 29, wherein said chromatography is undertaken by passing a solution of the phthalocyanine of formula (VII) in methanol through the ion exchange resin, then treating the eluate with ethyl ether to precipitate the phthalocyanine of formula (I) in chloride form, or by passing a solution of the phthalocyanine of formula (VII) in methanol/dimethylsulfoxide through the resin, then treating the eluate with ethyl ether to precipitate the phthalocyanine (I) which is then purified by dissolving in methanol and re-precipitating by adding ethyl ether.

31. A method for treating, by means of photodynamic therapy, bacterial infections caused by Gram-negative bacteria, alone or in the presence of other bacterial species, the method comprising subjecting said bacteria to a phthalocyanine compound of formula (I) as defined in claim 1.

\* \* \* \* \*